(12) United States Patent
Doubler et al.

(10) Patent No.: US 7,335,201 B2
(45) Date of Patent: Feb. 26, 2008

(54) POLYAXIAL BONE SCREW WITH TORQUELESS FASTENING

(75) Inventors: Robert L. Doubler, Ida, MI (US);
John E. Hammill, Rossford, OH (US)

(73) Assignee: Zimmer Spine, Inc., Minneapolis, MN (US)

( * ) Notice: Subject to any disclaimer, the term of this patent is extended or adjusted under 35 U.S.C. 154(b) by 443 days.

(21) Appl. No.: 10/673,680

(22) Filed: Sep. 26, 2003

(65) Prior Publication Data

US 2005/0070899 A1    Mar. 31, 2005

(51) Int. Cl.
*A61B 17/58* (2006.01)
(52) U.S. Cl. .......................................... 606/61; 606/72
(58) Field of Classification Search .................... 606/61
See application file for complete search history.

(56) References Cited

U.S. PATENT DOCUMENTS

| | | | |
|---|---|---|---|
| 255,428 A | 3/1882 | Graham | |
| 590,294 A | 9/1897 | Archer | |
| 4,378,187 A | 3/1983 | Fullerton | |
| 4,419,026 A | 12/1983 | Leto | |
| 4,653,969 A | 3/1987 | Summerlin et al. | |
| 4,684,284 A * | 8/1987 | Bradley, Jr. ................. | 403/320 |
| 4,822,223 A | 4/1989 | Williams | |
| 4,836,196 A | 6/1989 | Park et al. | |
| 4,854,304 A | 8/1989 | Zielke | |
| 4,887,595 A | 12/1989 | Heinig et al. | |
| 4,887,596 A | 12/1989 | Sherman | |
| 4,946,458 A * | 8/1990 | Harms et al. .................. | 606/61 |
| 5,002,542 A | 3/1991 | Frigg | |
| 5,110,244 A | 5/1992 | Garman | |
| 5,129,900 A | 7/1992 | Asher et al. | |
| 5,133,717 A | 7/1992 | Chopin | |
| 5,176,680 A * | 1/1993 | Vignaud et al. .............. | 606/61 |
| 5,324,150 A | 6/1994 | Fullerton | |
| 5,427,488 A | 6/1995 | Fullerton et al. | |
| 5,487,744 A | 1/1996 | Howland | |
| 5,549,608 A | 8/1996 | Errico et al. | |
| 5,569,247 A | 10/1996 | Morrison | |

(Continued)

FOREIGN PATENT DOCUMENTS

DE    197 20 782 A 1    11/1998

(Continued)

*Primary Examiner*—Eduardo C. Robert
*Assistant Examiner*—James L Swiger
(74) *Attorney, Agent, or Firm*—Wood, Herron & Evans, L.L.P.

(57) ABSTRACT

An adjustable spinal fixation system is composed of a collection of anchoring assemblies attached, via a variety of connectors, to spine-stabilizing rods. The anchoring assemblies include a linking member attached in a ball-and-socket fashion to a bone-engaging member that is adapted to engage a spinal bone of a patient. The linking member joins one of the included connectors to an associated bone-engaging member. The connectors are selectively attached to one of the stabilizing rods. The anchoring assemblies each include a support collar and a split retention ring that cooperate to allow adjustment of the bone-engaging member and corresponding connector during surgery. When surgery is complete, a linear engaging fastener cooperates with the support collar and split retention ring to maintain the relative position of the entire fixation system, preventing unwanted movement between the system components.

11 Claims, 5 Drawing Sheets

U.S. PATENT DOCUMENTS

| | | |
|---|---|---|
| 5,591,166 A | 1/1997 | Bernhardt et al. |
| 5,613,816 A | 3/1997 | Cabahug |
| 5,613,968 A | 3/1997 | Lin |
| 5,628,740 A | 5/1997 | Mullane |
| 5,653,765 A | 8/1997 | McTghe et al. |
| 5,716,357 A | 2/1998 | Rogozinski |
| 5,749,690 A | 5/1998 | Kutz |
| 5,788,443 A | 8/1998 | Cabahug |
| 5,800,108 A | 9/1998 | Cabahug |
| 5,800,435 A | 9/1998 | Errico et al. |
| 5,816,761 A | 10/1998 | Cassatt |
| 6,050,997 A * | 4/2000 | Mullane .................... 606/61 |
| 6,063,090 A | 5/2000 | Schlapfer |
| 6,090,111 A | 7/2000 | Nichols |
| 6,102,952 A | 8/2000 | Koshino |
| 6,162,234 A | 12/2000 | Freedland et al. |
| 6,179,512 B1 | 1/2001 | Gibson et al. |
| 6,187,005 B1 * | 2/2001 | Brace et al. .................. 606/61 |
| RE37,227 E | 6/2001 | Brodbeck |
| 6,254,602 B1 | 7/2001 | Justis |
| 6,537,005 B1 | 3/2003 | Denham |
| 6,602,255 B1 | 8/2003 | Campbell et al. |
| 6,623,485 B2 | 9/2003 | Doubler et al. |
| 6,866,664 B2 * | 3/2005 | Schär et al. .................. 606/61 |
| 2002/0114680 A1 | 8/2002 | Stoewer |
| 2003/0073996 A1 | 4/2003 | Doubler et al. |
| 2003/0149487 A1 | 8/2003 | Doubler et al. |
| 2004/0006342 A1 | 1/2004 | Altarac et al. |
| 2004/0162558 A1 * | 8/2004 | Hegde et al. .................. 606/61 |

FOREIGN PATENT DOCUMENTS

| | | |
|---|---|---|
| DE | 100 05 386 A 1 | 8/2001 |
| WO | WO 00/15125 | 3/2000 |

* cited by examiner

POLYAXIAL BONE SCREW WITH TORQUELESS FASTENING

FIELD OF THE INVENTION

This invention is directed to spinal implant systems and, in particular, to a multi-component adjustable implant system capable of maintaining a desired amount of torque between the skeletal bone and the implant.

BACKGROUND OF THE INVENTION

For individuals with spinal pathologies, the development of spinal fixation devices represents a major medical breakthrough. Surgically implanted fixation systems are commonly used to correct a variety of back structure problems, including those which occur as a result of trauma or improper development during growth. These fixation systems typically include one or more stabilizing rods aligned in a desired orientation with respect to a patient's spine. Additionally, anchoring screws are inserted into the patient's spinal bones, and a series of connectors is used to rigidly link the rods and anchors.

A variety of designs exist, with each design addressing various aspects of the difficulties that arise when one re-shapes an individual's spine to follow a preferred curvature. Unfortunately, known spinal implant systems often correct one set of problems only to create new ones.

Common to spinal implant systems is the necessity for proper anchoring to the bone so as to provide support for the aforementioned components. While bone screws are commonly used for anchoring, they are limited in their positioning due to the design of component pieces. Numerous patents are directed to component design in order to accommodate the bone screw, yet few patents are directed to bone screws that will accommodate existing component design. In most bone screw designs accommodation is made for applying anti-torque to the bone screw as other components are connected to the bone screws. This preserves the critical bone-screw interface which has been set when the screw is turned into the bone.

For this and other reasons, screws located in bone structure typically use a specially designed clamp to attach to a component such as an alignment rod. A problem with specially designed clamps is that bone structure cannot be determined until the patient's bone is exposed causing the necessity of a large inventory of various sized clamps to be on hand during surgery, of which the surgeon must search to find the right combination. Even if a clamp combination is predicted, insertion of the screw may still require angular insertion due to muscle or tender nerve locations. The result is a bone screw which exerts unpredictable forces upon attachment to component connectors. Further, any movement of muscle and other tissue increases the difficulty of the operation and can be a major trauma to a person.

A conventional bone screw consists of a single shaft with a coarse thread at one end for threading into the bone and a machine thread at the other end for coupling to components. Another type of bone screw has a U-shaped top which acts as a saddle for attachment to an alignment rod. If the screw is placed incorrectly for any reason, the rod clamp must be made to accommodate the position.

A number of patents exist which demonstrate the reliance on the saddle type screw support and various designs to accommodate the problem.

U.S. Pat. No. 5,133,717 sets forth a sacral screw with a saddle support. Disclosed is the use of an auxiliary angled screw to provide the necessary support in placing the screw in an angular position for improved anchoring.

U.S. Pat. No. 5,129,900 sets forth an attachment screw and connector member that is adjustably fastened to an alignment rod. An oblong area provided within each connector member allows minute displacement of the alignment rod.

U.S. Pat. No. 4,887,595 discloses a screw that has a first externally threaded portion for engagement with the bone and a second externally threaded portion for engagement with a locking nut. The disclosure illustrates the use of a singular fixed shaft.

U.S. Pat. No. 4,946,458 discloses a screw which employs a spherical portion which is adapted to receive a locking pin so as to allow one portion of the screw to rotate around the spherical portion. A problem with the screw is the need for the locking pin and the inability of the base screw to accommodate a threaded extension bolt.

U.S. Pat. No. 5,002,542 discloses a screw clamp wherein two horizontally disposed sections are adapted to receive the head of a pedicle screw for use in combination with a hook which holds a support rod at an adjustable distance.

U.S. Pat. No. 4,854,304 discloses the use of a screw with a top portion that is adaptable for use with a specially designed alignment rod to permit compression as well as distraction.

U.S. Pat. No. 4,887,596 discloses a pedicle screw for use in coupling an alignment rod to the spine wherein the screw includes a clamp permitting adjustment of the angle between the alignment rod and the screw.

U.S. Pat. No. 4,836,196 discloses a screw with an upper portion design for threadingly engaging a semi-spherical cup for use with a specially designed alignment rod. The alignment rod having spaced apart covertures for receipt of a spherical disc allowing a support rod to be placed at angular positions.

U.S. Pat. No. 5,800,435 sets forth a modular spinal plate assembly for use with polyaxial pedicle screw implant devices. The device includes compressible components that cooperatively lock the device along included rails.

U.S. Pat. No. 5,591,166 discloses an orthopedic bone bolt and bone plate construction including a bone plate member and a collection of fasteners. At least one of the fasteners allows for multi-angle mounting configurations. The fasteners also include threaded portions configured to engage a patient's bone tissue.

U.S. Pat. No. 5,569,247 discloses a multi-angle fastener usable for connecting patient bone to other surgical implant components. The '247 device includes fastening bolts having spherical, multi-piece heads that allow for adjustment during installation of the device.

U.S. Pat. No. 5,716,357 discloses a spinal treatment and long bone fixation apparatus. The apparatus includes link members adapted to engage patient vertebrae. The link members may be attached in a chain-like fashion to connect bones in a non-linear arrangement. The apparatus also includes at least one multi-directional attachment member for joining the link members. This allows the apparatus to be used in forming a spinal implant fixation system.

Another type of spinal fixation system includes rigid screws that engage the posterior region of a patient's spine. The screws are adapted with rod-engaging free ends to engage a support rod that has been formed into a desired spine-curvature-correcting orientation. Clamping members are often used to lock the rod in place with respect to the screws. Instead of clamping members, other fixation systems, such as that disclosed in U.S. Pat. No. 5,129,900, employ connectors that join the support rods and anchoring screws. The connectors eliminate unwanted relative motion between the rod and the screws, thereby maintaining the patient's spine in a corrected orientation.

Unfortunately, although these so-called "rigid screw" fixation systems can alter the curvature of a patient's spine, they can also be difficult to install. In this type of system, the anchoring screws must be secured in a region that is strong/rigid enough to support the characteristically-large loads typically transferred from the support rods. As a result, the number of suitable anchoring locations is limited. Typically, these screws are anchored into the posterior region of a patient's spinal column or into pedicle bone. With rigid screw systems, installation requires bending a support rod into a path that will not only correct the shape a patient's spine but that will also engage each of the installed anchoring screws. Achieving a proper fit between all of the components while contending with the constraints encountered during surgery is often difficult. In severe cases, a suitable fit may not be achieved and the surgery will be unsuccessful.

Additionally, the nature of the installation process required for rigid screw fixation systems often subjects the system components to pre-loading that unduly stresses the interface between the patient's bone and the employed anchoring screws. With these designs, as a patient moves about during daily life, the system components may become separated from the supporting bone. Corrective surgery to reattach anchoring screws exposes an already-weakened region to additional trauma and presents the risk of additional damage.

Other spinal fixation systems employ adjustable components. For example, U.S. Pat. No. 5,549,608 includes anchoring screws that have pivoting free ends which attach to discrete rod-engaging couplers. As a result, the relative position of the anchoring screws and rods may be adjusted to achieve a proper fit, even after the screw has been anchored into a patient's spinal bone. This type of fixation system succeeds in easing the rod-and-screw-linking process. This adjustment capability allows the screws to accommodate several rod paths. Unfortunately, some adjustable fixation systems tolerate only limited amounts of relative adjustment between components, operating best when loaded in one of several preferred arrangements. As a result, many prior art adjustable fixation systems are suitable for only a few situations.

Additionally, many adjustable fixation systems are prone to post-surgery component loosening. As a patient moves about during day-to-day living, his spine is subjected to a seemingly-endless amount of dynamic loading. Almost all activity requires some form of back motion; over time, this cyclic movement tends to work the components of many adjustable fixation systems loose.

Some adjustable spinal fixation systems include locking mechanisms designed for long-term, post-surgery securement of the system components. Although capable of being locked in place, these systems are often difficult to secure, requiring an excess of tools during the installation process. The need for extra tools, such as those required to shave, to apply anti-torque, or crimp key portions of a fixation system, increasing surgical risk by adding complexity and increasing the number of required steps. Although locking-component fixation systems exist, many of them unduly increase the dangers of back implant surgery to an unacceptable level.

Hardware-intensive fasteners are disclosed in U.S. Pat. No. 5,549,608, in which anchoring screws are fitted with wrenching flats that allow an anchoring screw to be attached to a patient's spinal bone with the flats being trimmed away once the screw is in place. Clamping nuts are then used to secure the anchoring screws to included stabilizing rods.

Additionally, many spinal fixation systems do not permit component repairs. If, for example, a threaded portion of a connecting member becomes stripped or cross-threaded, the entire connector must be slid off of the associated stabilizing rod. Often, such removal produces an undesirable "domino-effect," requiring that several connectors be slid off to allow removal of the damaged connector. Such requirements add unnecessary difficulty to an already-complex procedure.

The bone screws shown and described in U.S. Pat. Nos. 5,628,740 and 6,050,997 have a bone screw with a spherical cavity in the proximal end. A toggle bolt with a spherical distal end is inserted into the cavity in the bone screw. A collet is forced into the spherical cavity superior to the spherical end of the toggle bolt. A support collar or attachment cap is placed over the toggle bolt and tightened down. This forces the retention collet to engage the spherical portion of the toggle bolt and the inside of the spherical cavity locking the toggle bolt in a selected angular disposition. This system requires extremely accurate machining of the threaded components to result in an optimum frictional fit. Further, because the collet is a ring, with a fixed inner diameter, there is only one correct size for the spherical components. Finally, any deformation of the ring will lessen the over-all frictional contact by creating wrinkles or ridges on the collet.

U.S. Pat. No. 4,419,026 to Leto discloses a split ring camming internal locking device used with telescoping tubular members for transporting liquids. The ring is split for flexing to fit around the internal tube and for resiliently sealing against the external tube.

Thus, what is needed is a spinal fixation system that includes the advantages of known devices, while addressing the shortcomings they exhibit. The system should allow component adjustment during installation, thereby enabling satisfactory correction of a wide variety of spinal deformities. The system should also include a component locking mechanism that is simple and reliable. The system should also include mounting hardware that secures with a minimum of tools and that allows modular replacement of components damaged during installation. The system should also include tools and components for the locking mechanism developing a compression fit between components without additional torque on the bone-screw interface.

SUMMARY OF THE INVENTION

The present invention is a fastening system for bone screws used in spinal fixation systems for reshaping the spine of a patient. The bone screw has threads on one end for anchoring in the spine. The other end has a spherical connector with a conical cavity therein. The cavity has the larger diameter base of the cone toward the threaded end of the screw and a narrower mouth. The mouth of the conical cavity accepts the spherical end of a toggle bolt such that the toggle bolt and the bone screw are connected by a ball joint. To prevent disassembly of the bone screw and toggle bolt, an associated split retention ring locking mechanism is inserted in the conical cavity between the spherical end of the toggle bolt and the mouth of the cavity. The resilient split retention ring can be compressed to reduce its diameter for insertion through the mouth of the cavity and then expands to fill the conical cavity superior to the spherical end of the toggle bolt.

Because of the flexibility and resilience of the split retention ring, the mating parts do not require fine tolerances and are less expensive to make. Further, the split retention ring provides infinite adjustment of the locking pressure as the toggle bolt is pushed into the assembly. The system is modular, employing a collection of anchoring assemblies that are linked, via various connectors, to strategically-arranged stabilizing rods. The stabilizing rods are shaped and aligned to impart a preferred curvature to a patient's spine.

The anchoring assemblies are multi-piece units characterized by linking members that are joined in a ball-and-socket-type arrangement with a corresponding bone-engaging member. During use, the bone-engaging member is secured to a spinal bone and the linking member is secured to one of the stabilizing rods via a corresponding connector. The bone-engaging member may include coarse, external threads or have a hook-shaped end. Each anchoring assembly also includes a support collar that provides a secure interface between the bone-engaging member and associated connector. Each anchoring assembly also includes a securing ring and a locking insert that cooperate to prevent unwanted, post-installation motion within the anchoring assembly. The securing ring and locking insert also prevent unwanted relative motion between the anchoring assembly and associated connector.

The connectors are rigid structures adapted to link an associated anchoring assembly with one of the stabilizing rods. In one embodiment, the connectors are two-piece constructions that allow the connector to engage a stabilizing rod in a sandwich-type arrangement, permitting connector installation and removal that does not disturb adjacent connectors.

The stabilizing rods are rigid members shaped to form a spine-curvature-correcting path. Attaching each anchoring assembly, via connectors, to a stabilizing rod forces a patient's back into a surgeon-chosen shape. Stabilizing rods may be used singly, or in pairs, depending upon the type of correction required. The rods vary in size, but typically extend between at least two vertebrae.

The linear fastening system is capable of applying a tensile load to the linking member while supplying a clamping force for securing a connector. More specifically, the system utilizes a cooperating collet member and a compression ring member which are constructed and arranged to slip easily over a linking member while in a first release position. The collet member is constructed and arranged with an inner engaging surface and an outer tapered compression surface, the compression ring member being constructed and arranged with an inner tapered compression surface preferably conjugate in shape the outer surface of the collet member. The fastener system is secured by sliding the compression member in a linear overlapping fashion over the collet member, thereby utilizing the conical surfaces to compress the collet member and place a tensile load on the compression ring to grip the outer surface of the linking member. In this manner, the linear fastener system is capable of providing a secure connection between multiple components without the need to apply rotational torque to the assembly. The connection also allows full thread engagement and a locking connection without the need for plastic inserts or adhesives. When compared to traditional threaded fasteners, the dual conical compression surfaces allow very precise tensile loads to be applied to the shank member.

Accordingly, it is an objective of the present invention to provide a fastener system for polyaxial bone screws that is capable of securing multiple components into a single assembly without the need to apply rotational torque to the assembly.

An additional objective of the present invention is to provide a fastener system for polyaxial bone screws capable of linear engagement and disengagement.

It is a further objective of the present invention to provide a fastener system for polyaxial bone screws capable of providing linear engagement to externally threaded surfaces and the like.

It is another objective of the present invention to provide a polyaxial bone screw assembly for a spinal fixation system that permits component adjustment during installation, thereby enabling satisfactory correction of a wide variety of spinal deformities.

It is still another objective of the present invention to provide a linearly actuated compression connection between the components and the bone screw developing a strong secure fastening without additional torque on the bone screw.

It is an additional objective of the present invention to provide a bone screw assembly that includes a split ring locking mechanism that is simple and reliable.

It is a further objective of the present invention to provide a spinal fixation system that includes two-piece connectors that may be mounted along, and removed from, a support rod without requiring movement of adjacent connectors.

It is yet another objective of the present invention to provide a spinal fixation system that includes mounting hardware which requires a minimum number of tools.

It is also an objective of the present invention to provide a spinal fixation system that allows modular replacement of damaged components.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Figure 1:
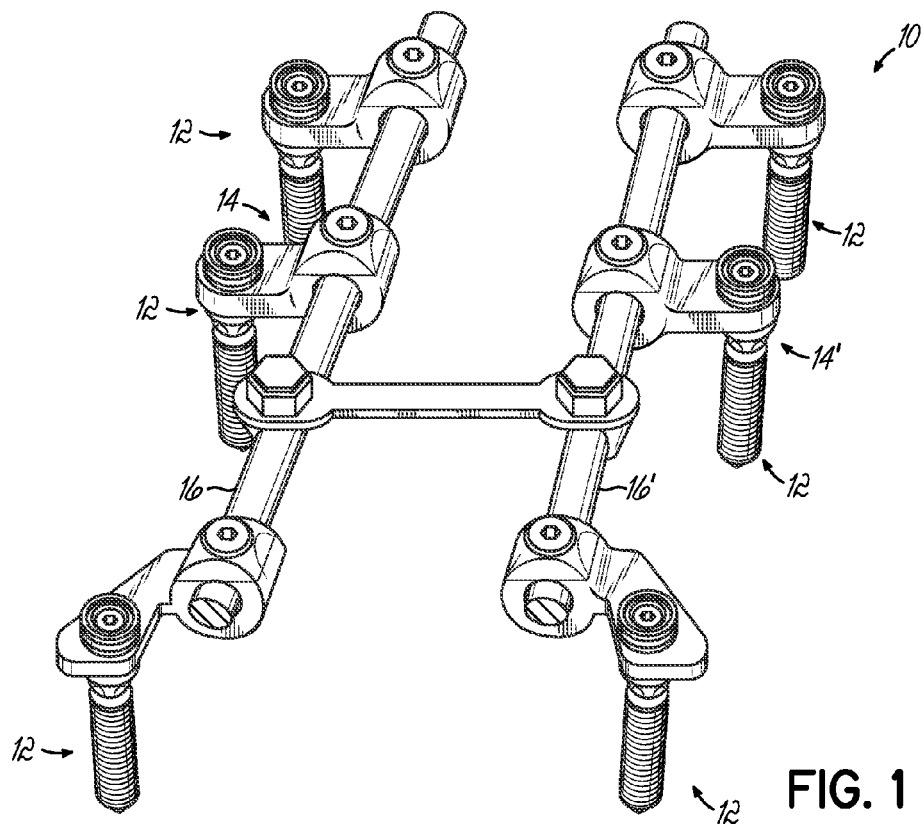
FIG. 1 is a pictorial view of the spinal fixation system of the present invention.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

Now with reference to FIG. 1, the spinal fixation system 10 of the present invention is shown. By way of overview, the fixation system 10 includes a collection of polyaxial bone-anchoring assemblies 12 that are joined via connectors 14, 14' to stabilizing rods 16, 16'. The specifics of the spinal fixation system 10 will now be discussed in more detail.

Figure 2:
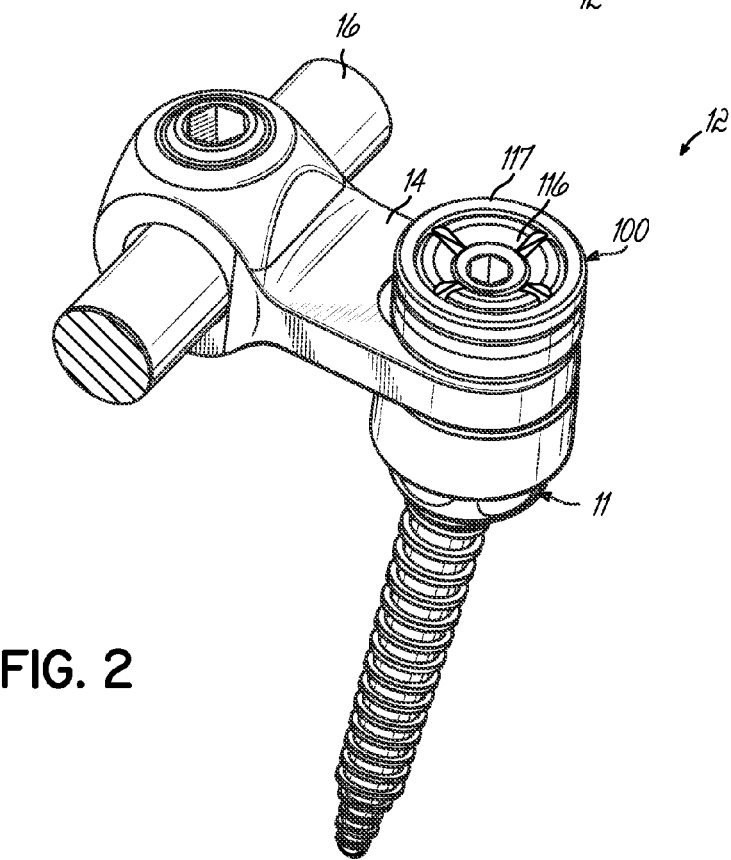
FIG. 2 is a perspective view of a toggle-type anchoring assembly used for spinal fixation utilizing the linear engaging fastener of the instant invention.
Figure 3:
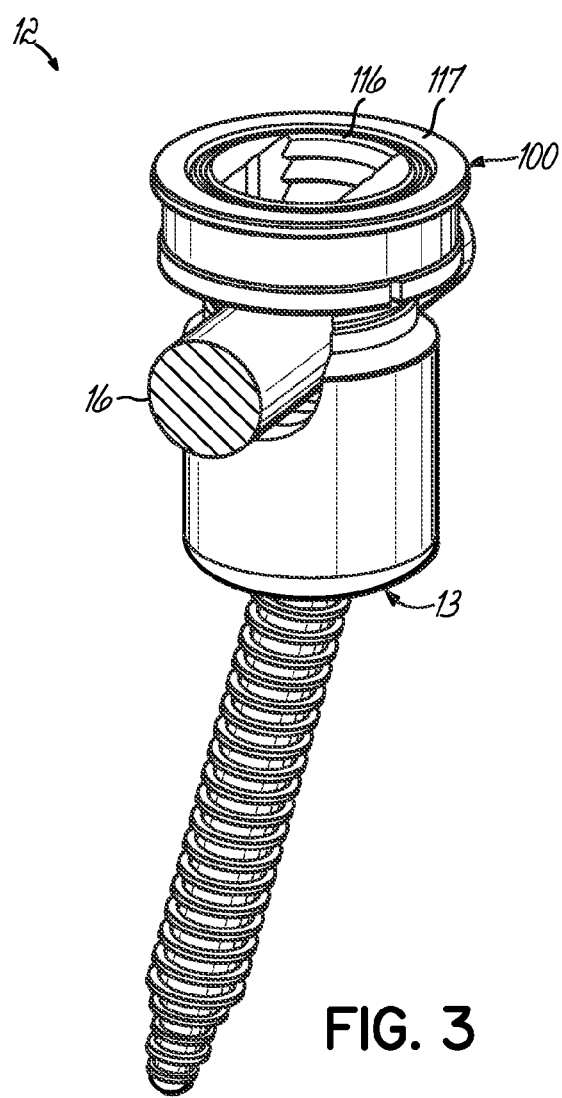
FIG. 3 is a perspective view of a saddle-type anchoring assembly used for spinal fixation utilizing the linear engaging fastener of the instant invention.
Figure 4:
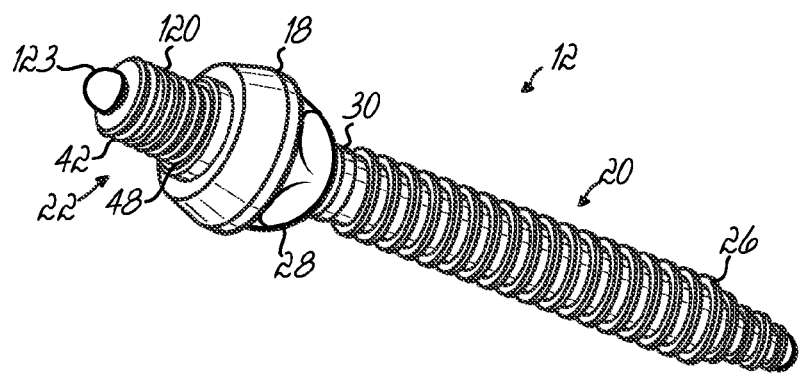
FIG. 4 is a perspective view of a toggle-type polyaxial bone-engaging screw having a support collar.
Figure 5:
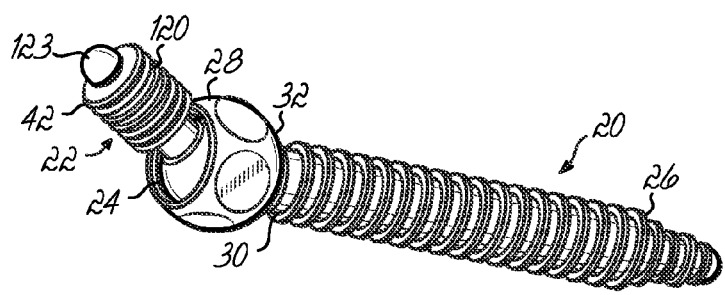
FIG. 5 is a perspective view of a toggle-type anchoring assembly having the support collar removed.
Figure 7:
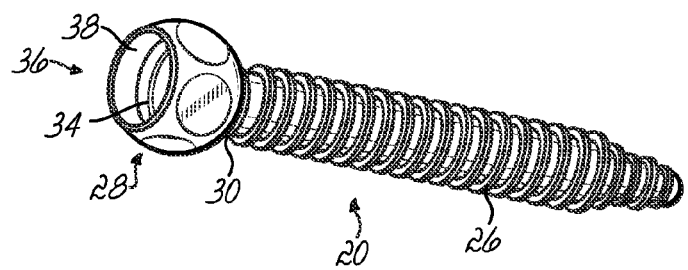
FIG. 7 is a pictorial view of a bone-engaging member from an anchoring assembly of the present invention.

With additional reference to FIGS. 2 and 3, two common types of polyaxial anchoring assemblies 12 are illustrated as the toggle bolt type polyaxial bone-screw 11 (FIG. 2) and the saddle type polyaxial bone-screw 13 (FIG. 3). Both types of polyaxial bone-screws are illustrated utilizing the linear engaging fastener 100 of the instant invention. FIG. 4 shows the toggle type polyaxial screw assembly 11 with an associated support collar 18. The support collar 18 is constructed and arranged to engage the outer spherical surface 32 of the pedicle screw 20 when a clamping force is applied to the toggle bolt 22. In addition to the support collar 18, each anchoring assembly 12 also includes a pedicle screw 20. As shown in FIGS. 4, 5 and 7, each pedicle screw 20 also includes a spherical end 28 spaced apart from the threaded end 26 by a neck portion 30. The exterior 32 of the pedicle screw spherical end 28 is preferably contoured for easy grasping. Within the toggle-type pedicle screw 11 the interior of the screw spherical end 28 forms a retention cavity 34, discussed below. The entrance 36 to the retention cavity 34 is characterized by a securing lip 38 that extends radially into the retention cavity 34.

Figure 8:
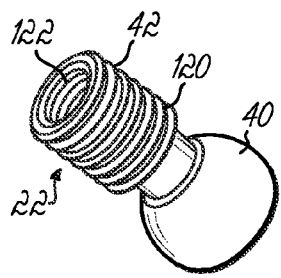
FIG. 8 is a pictorial view of a linking member from an anchoring assembly of the present invention.

Each toggle bolt 22, as shown in FIG. 8, includes a spherical end 40 and an opposite machined end 42. The spherical end 40 may be spherical, conical, or tapered. The machined end 42 may be formed with a helical thread, a series of parallel flanges, circular ramps, knurled, or otherwise altered to provide a gripping surface for the linear engaging fastener 100. While the term, machined, is used the bolt may be cast or molded or formed in other ways well known in the art. As shown in FIG. 5, the spherical end 40 of the toggle bolt 22 is shaped and sized to fit inside the pedicle screw retention cavity 34. Preferably, the interior of the retention cavity is substantially conical but slightly larger dimensions than the spherical contours of the toggle bolt spherical end 40.

Figure 9:
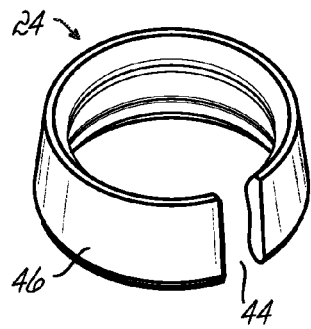
FIG. 9 is a pictorial view of a split retention ring of the present invention.

With reference to FIG. 9, the split retention ring 24 includes a gap 44 separating the opposite ends of the split retention ring main body 46. As seen in FIG. 5, the split retention ring 24 is used as a bracing means to secure the spherical end 40 of the toggle bolt 22 within the pedicle screw retention cavity 34. More specifically, after the toggle bolt spherical end 40 is placed within the pedicle screw retention cavity 34, the split retention ring 24 is pushed through the entrance 36 of the retention cavity 34 by reducing the gap 44 facilitating travel past the engagement lip 38, thereby bringing the split retention ring main body 46 to rest against the engagement lip by spring action resilience of the split retention ring 24.

With this arrangement, the split retention ring 24 allows pivotal movement of the toggle bolt 22 within the retention cavity 34, while preventing removal of the toggle bolt therefrom. Once the split retention ring 24 and toggle bolt 22 are in place, the machined end 42 of the toggle bolt is inserted through a passthrough aperture 48 of the support collar 18. This is shown in FIG. 4.

Once the toggle bolt 22 has been passed through the support collar passthrough aperture 48, the support collar 18 comes to rest against the pedicle screw ball end 28. Although several shapes are possible, the interior of the support collar 18 preferably has a contour that matches the exterior 32 of the pedicle screw ball end 28. This arrangement limits the relative motion possible between the support collar 18 and the toggle bolt 22, while allowing the toggle bolt ball end 40 to rotate freely within the pedicle screw retention cavity 34.

With additional reference to FIGS. 4 and 8, the toggle bolt may have internal threads 122 or a circular groove 123 around the perimeter of the toggle bolt 22. The internal threads allow the insertion of a threaded stem 110 for the linear compression tool 112, shown in FIG. 10. FIG. 11 illustrates utilization of the circular groove 123 for an alternate embodiment of the linear compression tool 112. Alternative constructions which allow attachment of a linear compression tool 112 may include, but should not be limited to cross drilled holes, internal circular grooves, flats formed on the end of the toggle bolt and the like.

Figure 10:
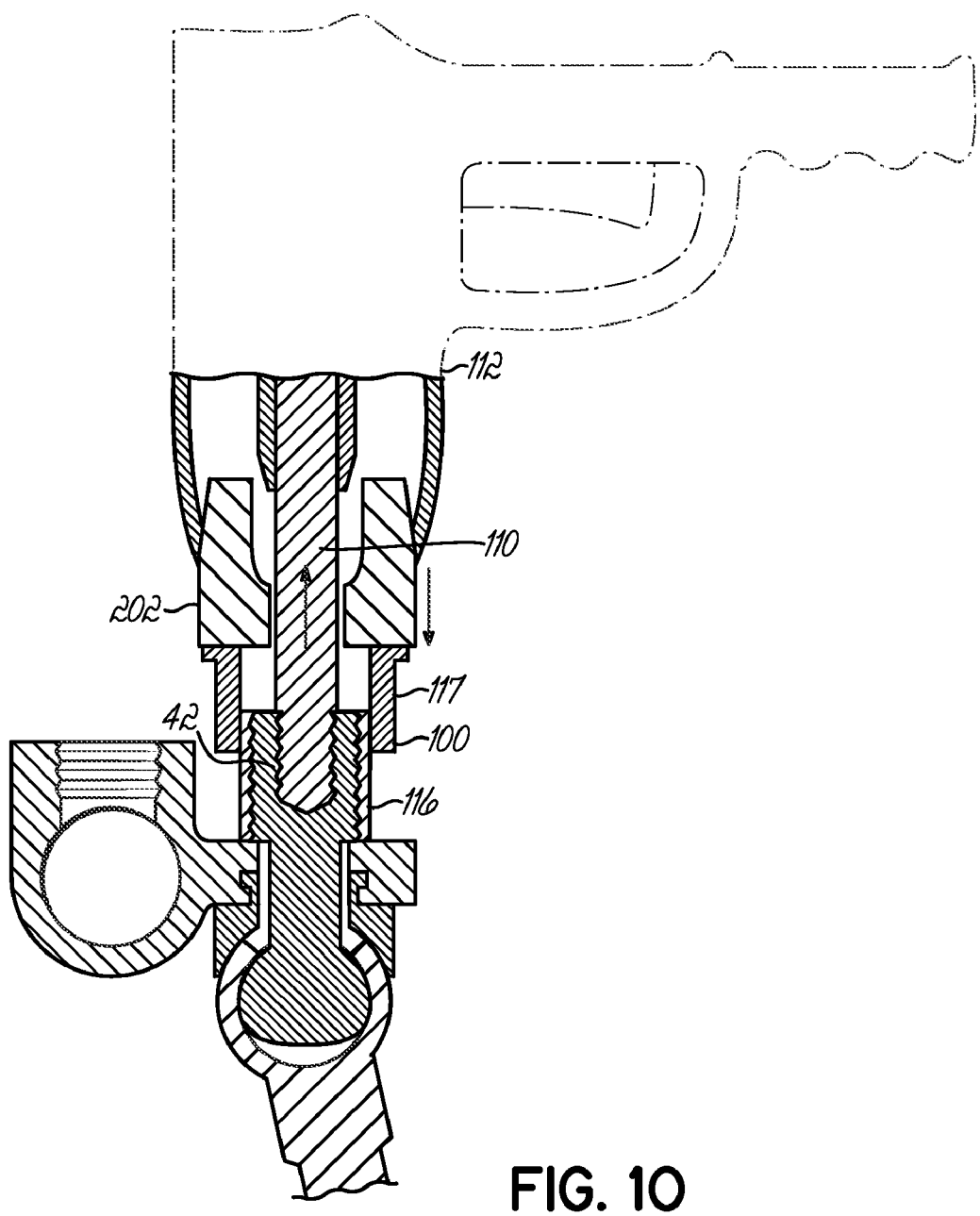
FIG. 10 is a section view illustrating one method of assembling the present invention.
Figure 11:
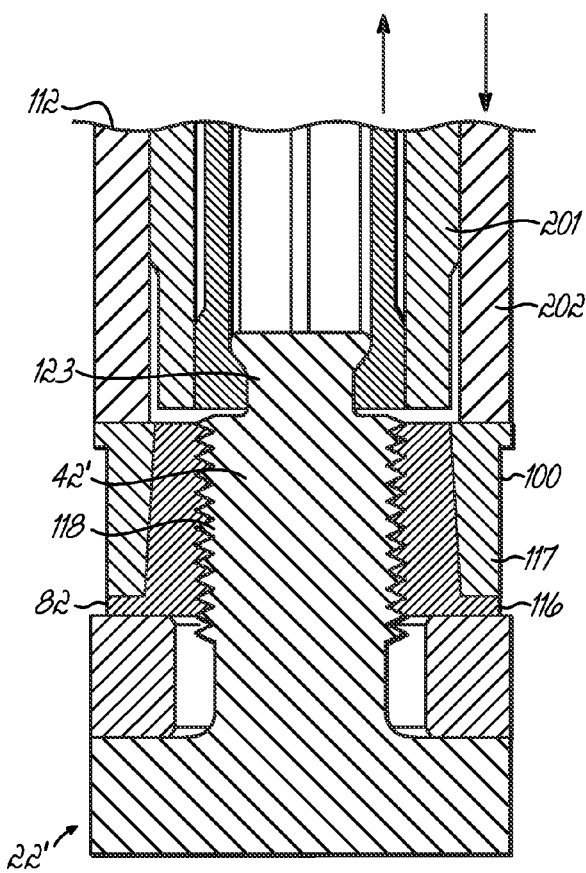
FIG. 11 is a section view illustrating one method of assembling the present invention.

Still referring to FIGS. 10 and 11, the linear tensile force and associated clamping force applied by an engaged linear fastener 100 on the toggle bolt machined end 42 forces relative longitudinal travel through the passthrough aperture 48 and causes the toggle bolt spherical end 40 to be forced against the split retention ring 24 (FIGS. 4-9) reducing the gap 44. Further equal and opposite linear engagement on the collet 166 by compression ring 117 forms a substantially rigid fit between the toggle bolt 22 and the pedicle screw 20 without torque being applied to the flexible joint or the bone-screw interface. With the collet 116 compressed appropriately, the toggle bolt machined end 42 is locked in place with regard to the right-facing straight connector attachment flange 82, and the toggle bolt spherical end 40 is locked in place within the pedicle screw retention cavity 34. In this state, the split retention ring is sandwiched between the exterior of the toggle bolt ball end 40 and the conical interior of the retention cavity 34. Since the split retention ring 24 is locked within the retention cavity 34 by the retention cavity engagement lip 38, relative motion between the toggle bolt spherical end and the pedicle screw 20 is prevented once the toggle bolt machined end 42 is locked in place by the collet 116 and compression ring 117. This results in a rigid link between the right-facing straight connector and the anchoring assembly 12.

Although the above description refers to joining an anchoring assembly 12 specifically to a right-facing straight connector, each of the one-piece connectors 14 and two-piece connectors 14' may be attached to an anchoring assembly in a similar manner. That is, right-facing offset connectors are attached by inserting a toggle bolt threaded end through the associated passthrough aperture; left-facing offset connectors are joined with an anchoring assembly by inserting a toggle bolt threaded end through an associated passthrough aperture; and left-facing straight connectors are attached to anchoring assemblies by inserting a toggle bolt threaded end through an associated passthrough aperture. In each case, the exterior connectors 120 of the inserted toggle bolt threaded end 42 are held in place by a compressed collet 116, as described previously.

Now with reference to FIGS. 10 and 11, alternate embodiments of an anchoring assembly 12' are shown with the linear compression tool 112 in place securing the toggle bolt 22' to pedicle screw 20'. In one of these embodiments, the toggle bolt 22' has an extension with a groove 123 beyond the threaded end 42' which serves as a bit to be connected to a linear compression tool 112, shown in FIG. 11. A collet 116 is placed about the threaded end 42'. The collet 116 has a cooperating internal surface 118 matching the configuration of the machined end 42'. The outer surface of the collet is tapered with a larger base resting on the flange 82. The groove 123 is connected to the tool 112 in a manner to apply linear force in a direction away from the screw 20'. The linear compression tool has an outer barrel 202 telescopically surrounding the extension 201. The tool 112 applies an equal and opposite linear force to the barrel and groove, simultaneously. The barrel 202 engages the tapered compression ring 117 to force the compression ring 117 over the collet 116 thereby completing a rigid compression fit. The toggle bolt 22' may be constructed having an integrally formed extension with a frangible area (not shown) adjacent the machined end 42' or alternatively a threaded stem may be secured to the threaded internal cavity 122. Once the linear engagement is secured, the barrel of the tool 112 can be used to sever the extension or the threaded stem may be removed manually.

Figure 6:
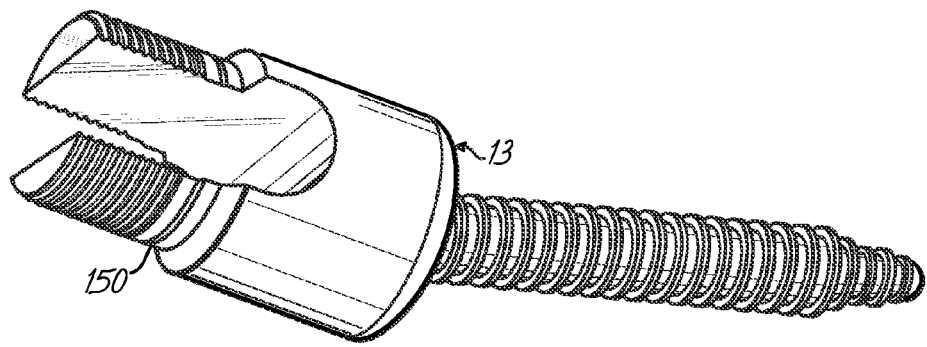
FIG. 6 is a perspective view of a saddle-type polyaxial bone-engaging screw.
Figure 12:
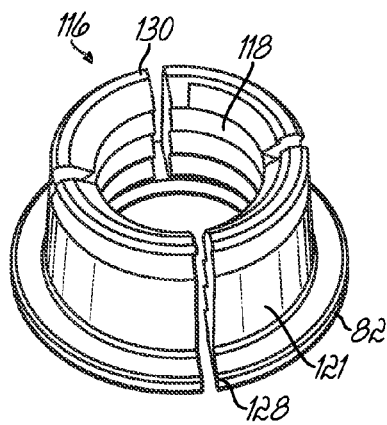
FIG. 12 is a pictorial view illustrating one embodiment of the collet utilized for linear engagement of the present invention.
Figure 13:
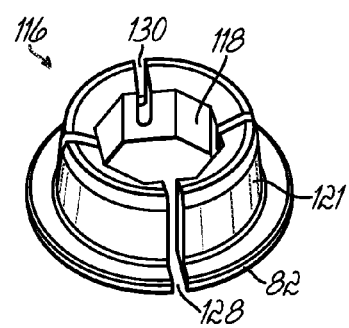
FIG. 13 is a pictorial view illustrating one embodiment of the collet utilized for linear engagement of the present invention.
Figure 14:
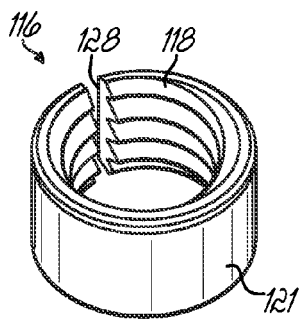
FIG. 14 is a pictorial view illustrating one embodiment of the collet utilized for linear engagement of the present invention.

The collet member 116 shown in FIGS. 12 through 14 is slid or loosely threaded over the external machined end 42 of the linking member 22 or a U-shaped saddle member 150 generally shown in FIGS. 4 through 6. To facilitate compression, the collet member is provided with at least one slot 128 extending completely through the collet and preferably includes a plurality of partial slots 130. The external surface 121 of collet member 116 is tapered or conical in form. The internal gripping surface 118 of collet member 116 is generally constructed and arranged to have a conjugate surface to the machined surface 42 of the linking member 22 or the U-shaped saddle member 150 for cooperative engagement therebetween. In addition, the internal gripping surface 118 of the collet member may be constructed and arranged to exert a tensile force on the toggle or saddle members when compressed. This construction allows precise clamping forces to be applied to an assembly, allows full surface engagement between the toggle or saddle member and the collet member, and facilitates a locking connection without inserts or adhesives. The collet member 116 may also include a flared base 82 suitable to distribute a clamping force over a wide area or provide a load bearing surface for adjacent components.

Figure 16:
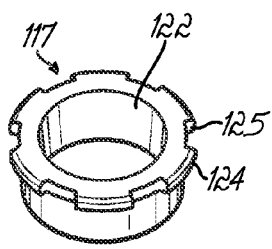
FIG. 16 is a pictorial view illustrating one embodiment of the compression ring utilized for linear engagement of the present invention.
Figure 17:
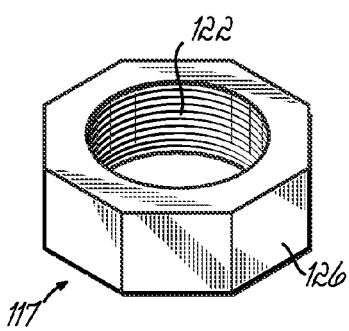
FIG. 17 is a pictorial view illustrating one embodiment of the compression ring utilized for linear engagement of the present invention.
Figure 15:
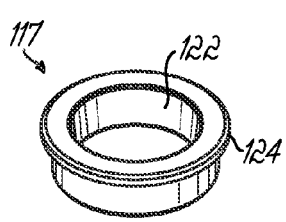
FIG. 15 is a pictorial view illustrating one embodiment of the compression ring utilized for linear engagement of the present invention.

Referring to FIGS. 15-18, the compression ring 117, shown in FIGS. 15 through 17, has a tapered interior surface 122 which is complementary to the taper of collet member 116. The compression ring 117 may be constructed with a flange 124 about the upper surface. The flange 124 may have optional lugs 125 formed in a C-shape for engaging an extractor (not shown) used to remove or disconnect the coupling. The flange may also have optional wrench flats 126 for engaging wrenches and/or sockets that are well known in the art.

Referring to FIGS. 1 through 17, the spinal fixation system 10 is preferably formed from rigid, biocompatible materials. One such preferred material is titanium; however, other materials well known in the art may also be used.

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

What is claimed is:

1. A kit for creating a spinal fixation assembly comprising:
   a polyaxial bone screw having a first end constructed and arranged for threaded engagement in a spinal bone by application of an effective amount of rotational torque, and a second end constructed and arranged for swivelable attachment of a linking member;
   a linking member having a first end constructed and arranged for attachment of a connecting member and a second end constructed and arranged for swivelable attachment to said second end of said bone screw;
   a connecting member constructed and arranged for adjustable positioning about said linking member first end; and
   a linear fastener constructed and arranged to provide positive compressive attachment of said connecting member and said linking member first end;
   whereby a non-rotational, linear force is applied to said linear fastener to effectuate a coupling of said fastener about said linking member first end to produce and maintain a clamping force effective to produce a spinal fixation assembly having a fixed orientation.

2. The spinal fixation assembly kit of claim 1 wherein said second end of said bone screw is substantially spherical having a surface which is constructed and arranged to cooperate with a support collar, said support collar including a substantially spherical first surface and a generally flat second surface, whereby engagement of the linear fastener supplies a clamping force to said support collar for locking said linking member in a chosen orientation.

3. The spinal fixation assembly kit of claim 2 wherein said linear fastener includes:
   a collet member having a base end, a top end, an inner engaging surface, and an outer tapered compression surface positioned about a central axis;
   a compression ring member having a base end, a front end, an inner tapered compression surface, and an outer surface positioned about a central axis;
   wherein said inner tapered compression surface of said compression ring member is constructed and arranged for coaxial alignment and overlapping engagement with respect to said outer tapered compression surface of said collet member, said compression ring member linearly traversable with respect to said outer tapered surface of said collet member between a first release position and a second engaged position, wherein said collet member is placed over said first end of said linking member in said first release position and wherein said engaged position results in said cooperating tapered surfaces compressing said collet member and tensilely loading said compression ring member thereby supplying said clamping force and gripping the outer surface of said linking member.

4. The spinal fixation assembly kit of claim 3 wherein said first end of said linking member includes a tensioning means; wherein said tensioning means is constructed and arranged to allow said linking member to be tensilely loaded prior to linear traversal of said compression ring member to said engaged position with respect to said collet member.

5. The spinal fixation assembly kit of claim 4 wherein said tensioning means includes at least one groove extending around the circumference of said first end of said linking member, wherein said at least one groove is constructed and arranged for gripping and placing a tensile load on said linking member prior to linear traversal of said compression ring member into said engaged position with respect to said collet member.

6. The spinal fixation assembly kit of claim 4 wherein said tensioning means includes at least one internal bore extending inwardly from said first end along a longitudinal centerline of said linking member, wherein said at least one internal bore is constructed and arranged for gripping and placing a tensile load on said linking member prior to linear traversal of said compression ring member into said engaged position with respect to said collet member.

7. The spinal fixation assembly kit of claim 4 wherein said tensioning means includes a frangible stem, whereby said frangible stem is severed from said first end of said linking member when said linking member reaches a predetermined tension, wherein said frangible stem is severed subsequent to linear traversal of said compression ring member into said engaged position with respect to said collet member.

8. The spinal fixation assembly kit of claim 6 wherein said internal bore includes threads.

9. The spinal fixation assembly kit of claim 1 wherein said first end of said bone screw has screw threads to engage said bone.

10. A kit for creating a spinal fixation assembly comprising:
   a bone achor having a first end constructed and arranged for engagement in a spinal bone, and a second end;
   a linking member having a first end and a second end, said second end of said bone anchor and said second end of said linking member constructed and arranged for swivelable attachment therebetween;
   a connecting member constructed and arranged for adjustable positioning about said first end of said linking member; and
   a linear fastener constructed and arranged to secure said connecting member to said first end of said linking member, whereby a non-rotational, linear force is applied to said linear fastener to effectuate a coupling of said fastener about said first end of said linking member to produce and maintain a clamping force between said linking member and said bone anchor effective to fix said connecting member to said linking member in a fixed orientation and to fix said linking member to said bone anchor in a fixed orientation.

11. The spinal fixation assembly kit of claim 10 wherein said bone anchor is a polyaxial bone screw.

* * * * *